(12) United States Patent
Lustenberger

(10) Patent No.: US 7,192,185 B2
(45) Date of Patent: Mar. 20, 2007

(54) METHOD OF AND EQUIPMENT FOR CHECKING SUPPORT MEANS

(75) Inventor: Martin Lustenberger, Villars sur Glane (CH)

(73) Assignee: Inventio AG, Hergiswil (CH)

( * ) Notice: Subject to any disclaimer, the term of this patent is extended or adjusted under 35 U.S.C. 154(b) by 92 days.

(21) Appl. No.: 10/974,607

(22) Filed: Oct. 27, 2004

(65) Prior Publication Data

US 2005/0063449 A1   Mar. 24, 2005

(30) Foreign Application Priority Data

Nov. 4, 2003   (EP) .................................. 03405790

(51) Int. Cl.
*G01N 3/18* (2006.01)
*G01N 25/72* (2006.01)
(52) U.S. Cl. ............................... 374/50; 374/57; 374/5
(58) Field of Classification Search ................ 374/49, 374/50, 15
See application file for complete search history.

(56) References Cited

U.S. PATENT DOCUMENTS 4,486,103 A * 12/1984 Ando ............................ 374/5

6,147,931 A * 11/2000 Seaman et al. ............. 367/153
6,205,867 B1 * 3/2001 Hayes et al. ............ 73/862.391

FOREIGN PATENT DOCUMENTS

| EP | 1 022 376 | | 7/2000 |
|---|---|---|---|
| GB | 2 169 702 | | 7/1986 |
| JP | 55010517 A | * | 1/1980 |
| JP | 58009043 A | * | 1/1983 |
| JP | 02233486 A | * | 9/1990 |
| JP | 05332962 A | * | 12/1993 |
| WO | WO 03/043926 | | 5/2003 |
| WO | WO03/077393 | | 9/2003 |

* cited by examiner

*Primary Examiner*—Gail Verbitsky
*Assistant Examiner*—Mirellys Jagan
(74) *Attorney, Agent, or Firm*—Butzel Long

(57) ABSTRACT

A method and equipment for checking a support device such as used in an elevator installation. The method and equipment detects reductions in cross-section of the tensile supports in the support device by heating the tensile supports with electrical current flow and determining the temperature at surface of surrounding sheathing. An increase in the temperature from an original measurement is an indicator of damage to the tensile supports.

17 Claims, 4 Drawing Sheets

METHOD OF AND EQUIPMENT FOR CHECKING SUPPORT MEANS

BACKGROUND OF THE INVENTION

The present invention relates to a method for checking a support means and to equipment for checking a support means in an elevator installation.

Known support means are cables or belts. Belts consist of several tensile supports that are embedded in a common sheathing. The form of the belt is, as a rule, flat. This means the tensile supports are arranged adjacent to one another at a slight spacing and the sheathing surrounds this tensile support belt and fills out the intermediate spaces formed by the spacings of the tensile supports. The tensile supports are produced by known technology from steel material or steel-like materials mostly as strands and are usually electrically conductive.

Support means of the above-described form are also increasingly used in elevator construction. Thus, a corresponding belt is shown in the PCT published patent application WO 03/043926.

A special requirement results, in the case of use of support means of that kind, with the checking of the support means. The support means are exposed to various influences in use. They are subject to a continuous wear. They are exposed to an increased risk of breakage of individual wires at, in particular, deflection points of the support means, for example when the support means is guided over rollers, or the tensile supports can also be damaged due to extraordinary events, such as assembly influence, impacts and corrosion. These influences reduce the load-bearing cross-section and thus the tolerable load-bearing force of the support means and can in the extreme case lead to failure of the support means.

In currently usual installations traditional steel cables are used without sheathing. These steel cables can be checked visually or by means of a magnetic induction method, wherein readiness for discard is determined according to the DIN15020-2 standard.

SUMMARY OF THE INVENTION

An object of the present invention is to provide a method and equipment which allow checking of a support means for damage of tensile supports without in that case damaging the support means.

According to the present invention use is made of the physical effect that an electrical conductor heats up when an electric current flows through it. This heating is dependent on the conductor cross-section or on the resistance of the conductor and on the thermal dissipation through the surroundings of the conductor. If a conductor has, in a length section, a reduced cross-section the resistance increases in the corresponding length section, which causes two effects.

Firstly, the voltage over the conductor has to be increased in order to achieve a specific current flow or the flow of current reduces in correspondence with the increase in resistance.

Secondly, the conductor heats up in the length section with the cross-sectional reduction than in the remaining region with unchanged cross-section.

The two effects are, according to the present invention, utilized in order to be able to undertake a reliable assessment of the readiness of a support means for discard.

A tensile support of the support means is subjected at least periodically to an electric measuring current and the temperature of the support means is established.

The required measuring current is produced by a current control. The measuring current heats the loaded part. In the case of an undamaged tensile support, the heating is uniform over the entire length of the support means. If damage is present in the tensile support, the cross-section in the corresponding length section reduces and the temperature increases in this length section. The temperature is measured, preferably at the surface of the support means, by a temperature measuring apparatus. There is thus established a temperature increase and, on the basis of the increase, the degree of damage assessed or the readiness for discard ascertained.

The equipment or the method enables assessment of the intensity of damage as well as determination of the location of the damage. Moreover, the equipment can be economically procured in the market and the method is simple in use.

This equipment is principally optimized for use in elevator construction.

DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
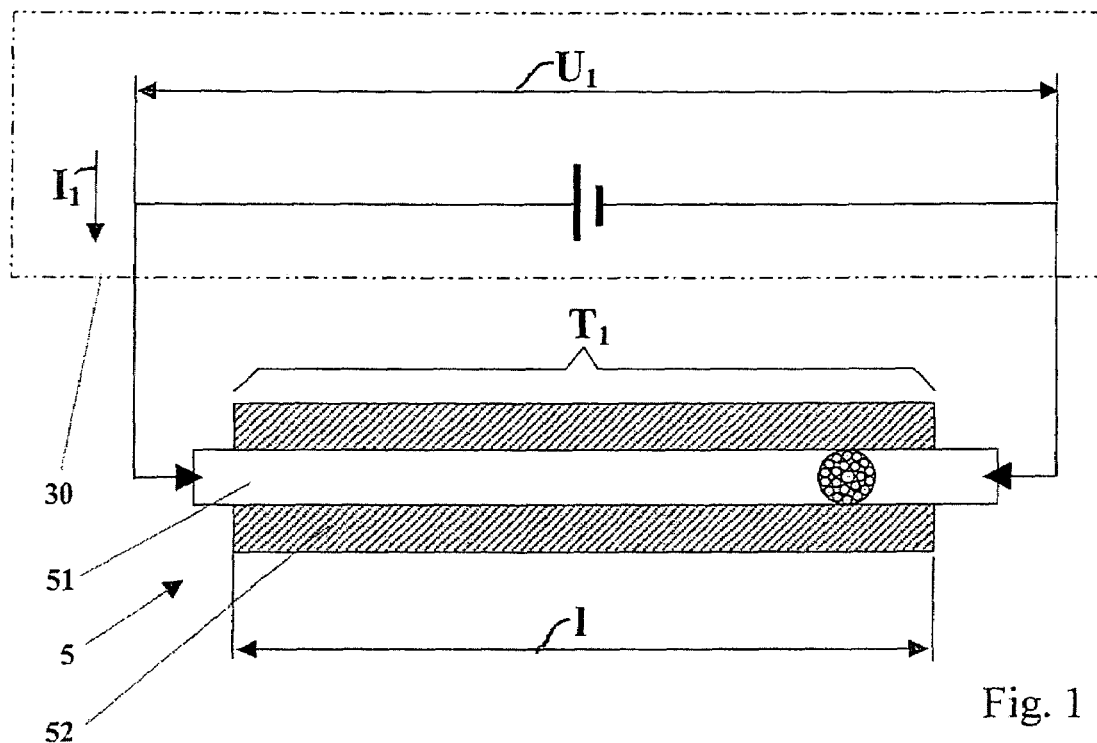
FIG. 1 is schematic view of a theoretical model of an intact support means in longitudinal section.
Figure 2:
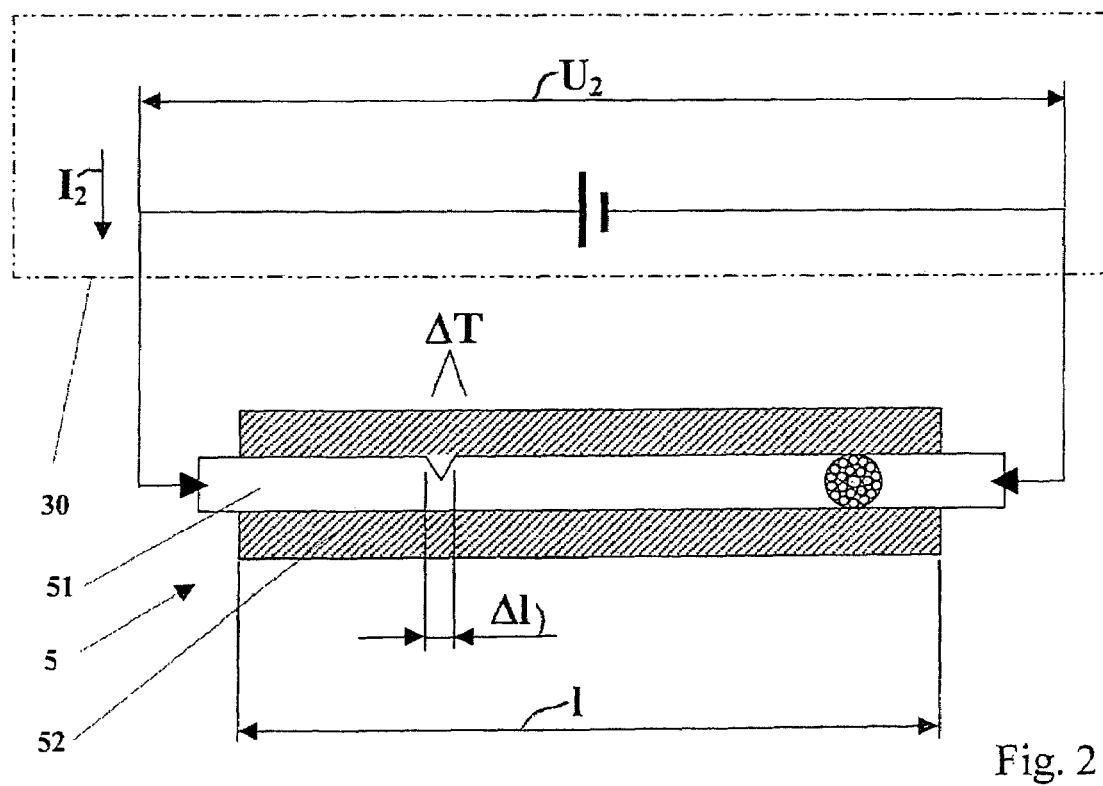
FIG. 2 is a view similar to FIG. 1 showing a theoretical model of a damaged support means in longitudinal section.

The present invention is illustrated in schematic form in FIGS. 1 and 2. A support means 5 includes a tensile support 51. The tensile support 51 is produced from electrically conductive material or is electrically conductive as a whole. The tensile support 51 is enclosed by a sheathing 52 or embedded in this sheathing 52. The sheathing 52 consists of a substantially electrically insulating material such as, for example, polyurethane. It insulates the individual tensile supports 51 substantially from one another. The support means 5 has a length 1 appropriate to the use.

In the examples illustrated in FIGS. 3 to 7 the support means 5 consists of twelve of the tensile supports 51, which in turn are stranded in the form of cable strands from individual steel wires. In the shown example the diameter of the tensile support 51 amounts to approximately 1.5 millimeters to 2.0 millimeters. The tensile supports 51 are spaced from one another and sheathed as a whole by a plastic material. The sheathing 52 substantially insulates the individual tensile supports 51 from one another and forms a functionally appropriate surface which has, for example, specific material characteristics or surfaces in order to transmit a driving force to the support means 5. In the shown example the sheathing 52 is smooth at both sides or can be grooved at one side and smooth on the other side. The overall width of the support means 5 amounts, in the shown example, to approximately 23 to 35 millimeters and the thickness amounts corresponding to 3 to 7 millimeters.

For carrying out the checking of the support means 5 the tensile supports 51 are subjected to a measuring current by means of a current control 30. The individual tensile supports 51 have a resistance "R" of approximately 0.16 Ωm. According to FIG. 1 a measuring current of $I_1=5$ A thus results in the case of a voltage of $U_1=0.8$ V/m applied by the current control 30. This measuring current produces, with consideration of the heat radiation and the support means embodiment shown by way of example, a surface temperature $T_1$ of approximately 42° C. when the tensile support 51 is intact.

The measured values above are examples. Depending on the construction, other dimensions and correspondingly other values are possible.

If the tensile support 51 is damaged as apparent from FIG. 2, there is an increase, in the relevant length section Δ1 of the tensile support 51, in the resistance to current flow and correspondingly the power loss over this length section, which causes an increase in the surface temperature. With the characteristic example, a cross-sectional reduction of 8%, for example, causes a temperature rise ΔT of 0.7° K at the surface of the damage. In the case of a cross-sectional reduction of 30%, the surface temperature increases by approximately 7° K.

According to the present invention this physical effect is used in order to check the support means 5 for damage. The tensile support 51 of the support means 5 is provided with a measuring current by the current control 30. The temperature of the support means 5 over the entire critical length of the support means is measured preferably by means of a temperature measuring apparatus 40 (FIG. 4) and on the basis of an established temperature change with respect to the preceding length section and/or with respect to the mean value of the temperature measurement over the entire length of the support means 5 a warning report is generated and the location of the damage can, in the case of need, be determined precisely. On the basis of the established temperature difference a cross-sectional reduction in the tensile support 51 can be recognized, the resulting reduction in load-bearing force can be reliably assessed and correspondingly the readiness for discard can be recognized.

The advantages of the present invention are that the support means can be precisely assessed with respect to its state, that the support means 5 is not damaged in the case of checking, that the apparatus to be used can be obtained in simple manner commercially and that the use is simple.

Preferably the temperature is substantially established at the surface of the support means. Instead of the temperature measurement there can also be used a sheathing 52 or an appropriate layer which changes color in dependence on temperature that can be worked into the surface of the sheathing 52. Damage to one of the tensile supports 51 can thereby be visually recognized particularly efficiently without need for the temperature measuring apparatus 40.

For test purposes a corresponding film, which changes color in dependence on temperature, can also be applied only temporarily to the surface of the sheathing 52.

In a variant, a temperature detector can be located in the sheathing 52 of the support means 5. The temperature detector measures the temperature in the sheathing of the support means.

Figure 3:
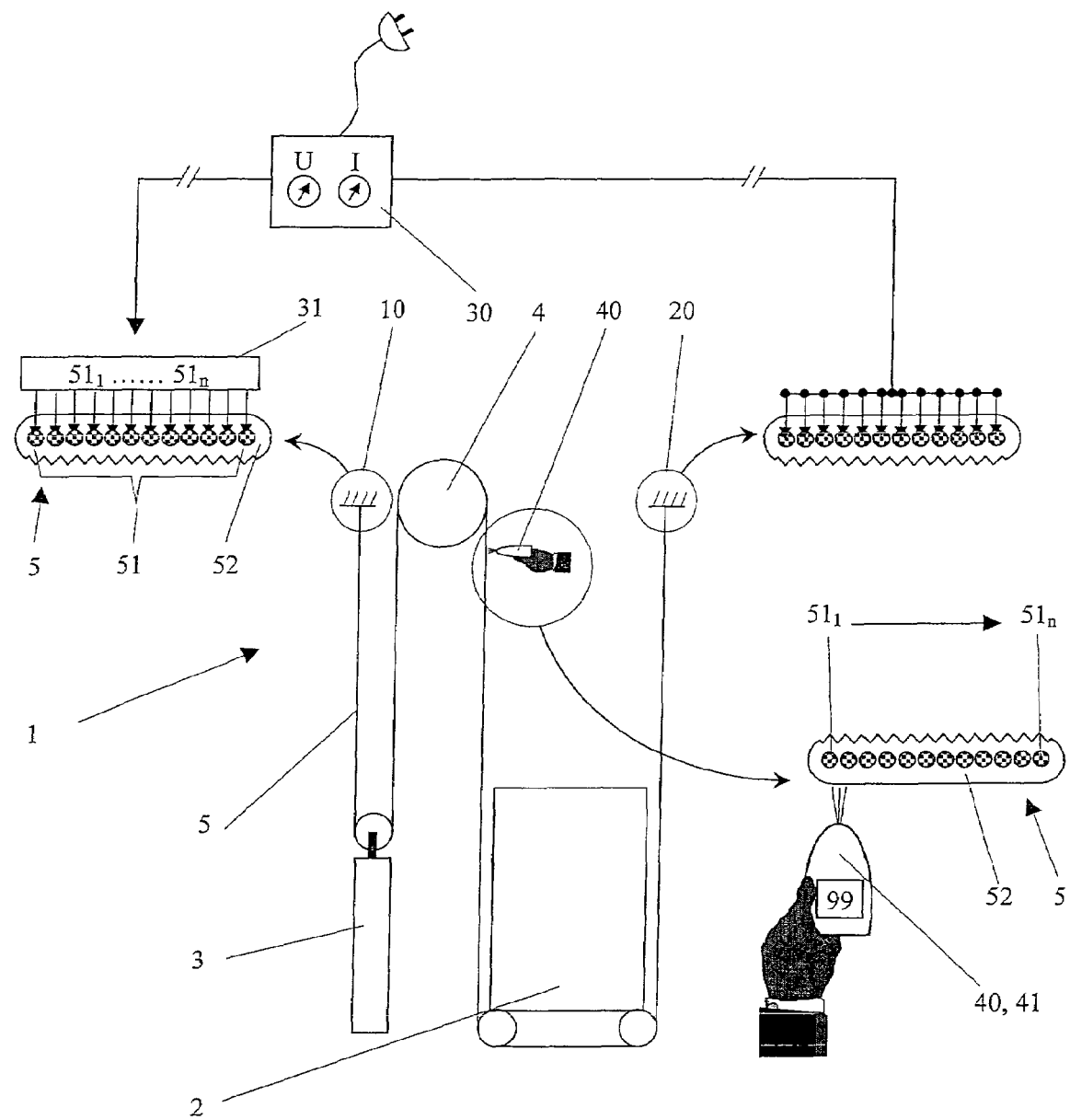
FIG. 3 is a schematic diagram of equipment for establishing the readiness for discard of a support means in an elevator installation.

In the case of the use shown in FIG. 3, the equipment for checking the support means 5 is illustrated, by way of example, for the example of an elevator installation 1 with a suspended car 2 and a suspended counterweight 3. The tensile supports 51 of the support means 5 are connected at a first support means end 10 by means of a switching element 31 to be individually switchable to a pole of the current control 30. At a second support means end 20 the tensile supports 51 are electrically conductively connected and are connected in common with the opposite pole of the current control 30.

By means of setting the supply voltage (U) and/or a pulse control a medium measuring current (1) is set and a first tensile support $51_1$ is flowed through by this measuring current, whereby the measuring current produces a heating of the first tensile support $51_1$ and its surrounding sheathing 52.

The temperature of the support means 5 is measured by means of the temperature measuring apparatus 40 at a point which corresponds with the arrangement of the first tensile support $51_1$ connected in accordance with the switch setting of the switching element 31. The illustrated temperature measuring apparatus 40 measures the temperature of the support means 5 at the surface of the sheathing 52. The measuring is carried out in the illustrated example in the vicinity of a drive motor 4, wherein the drive motor 4 moves the elevator installation or the support means forwardly at a low speed. If now a change in the surface temperature is established, the drive motor 4 is stopped and the point can be directly assessed or can be marked for later observation. As a rule, the ascertained change is stored, which can be carried out manually, by means of an electronic memory of the measuring apparatus or by means of a data writer connected with the measuring apparatus.

After checking of the first tensile support $51_1$ has been carried out, there is switching by means of the switching element 31 to a next tensile support $51_2$ and the checking of the next tensile support $51_2$ is carried out in correspondence with the checking of the first tensile support $51_1$. Checking of the following tensile supports . . . $51_n$ is carried out by continuing or repeating the checking sequence.

A random reduction in the load-bearing cross-section of the individual tensile supports 51 and thus readiness of the support means 5 for discard can now be evaluated on the basis of the established temperature deviations. The association table or the dependence function of the remaining cross-section with respect to temperature deviation is ascertained usually on the basis of pattern elements and established.

Advantageously the new state of the support means 5 or of the tensile support 51 is established and fixed after initial installation. The first measuring is carried out analogously to the sequence described beforehand. Thus, for example, the voltage required for attainment of the measuring current is permanently stored as a new voltage. In the case of checking the support means 5 or the tensile supports 51 there can now be ascertained, additionally to establishing the load-bearing residual cross-section, the general state of the tensile support 51 and thus of the support means 5 in accordance with the following:

that the measuring current flow cannot be achieved has the meaning that the relevant tensile support 51 is interrupted, i.e. destroyed;

if the requisite supply voltage is higher than the new voltage this means that the cross-section is reduced as a whole or that wear is present;

if the requisite supply voltage is lower than the new voltage this means that a parallel connection is present. This means that the tensile support 51, for example, is in contact with an adjacent tensile support. In this case on measuring the surface temperature at the point of the parallel connection a permanent reduction in the temperature at the surface of the support means can be established.

The listed possibilities of evaluation represent economic and simple possibilities of undertaking a comprehensive checking and evaluation of support means. The support means is not damaged by the checking, which enables further usage.

In the illustrated example according to FIG. 3, a manually settable transformer is used for setting the measuring current at the current control 30. A manual temperature measuring apparatus 40, i.e. a surface thermometer 41, is similarly used for measuring the temperature. Evaluation of the measurement results is accordingly similarly undertaken manually. Thus a simple and economic method is available in order to check the individual tensile supports 51 of the support means 5 and to evaluate the readiness of the support means 5 for discard. The transformer and thermometer are readily available equipment used in industrialized fields.

Figure 4:
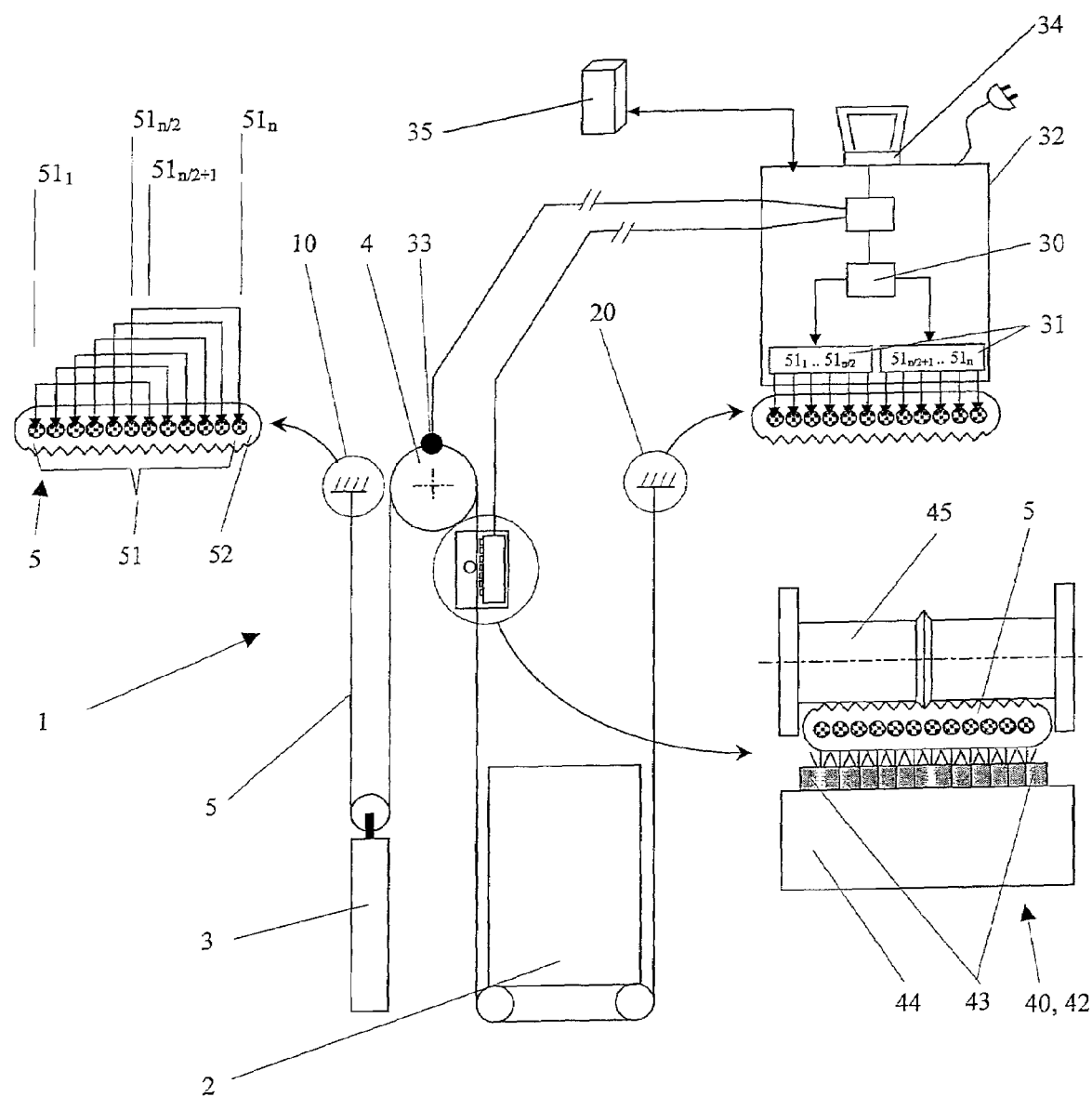
FIG. 4 is a schematic diagram of a second example of equipment for establishing the readiness for discard of a support means in an elevator installation.

FIG. 4 shows an automated overall solution for checking the support means 5 in the elevator installation 1.

The tensile supports 51 of the support means 5 are connected together in pairs at the first end of the support means 10 so that two spaced tensile supports $51_1$, $51_{n/2+1}$ are connected in series. At the second end of the support means 20 the tensile supports 51 are led, in correspondence with the connecting together of the first end of the support means 10, to the switching element 31 and from this switching element 31 to the current control 30. The switching element 31 and the current control 30 are in this example integrated in a checking unit 32 or are controlled at least by the checking unit 32.

Figures 6A, 6B:
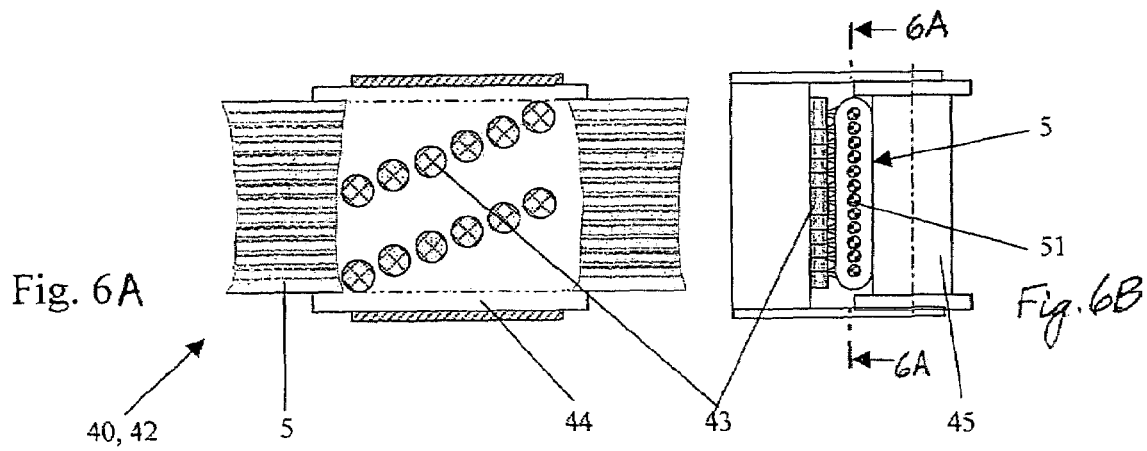
FIG. 6A is a cross-sectional view taken along the line 6A—6A in FIG. 6B showing an example of a temperature measuring apparatus according to the present invention for establishing the surface temperature of a support means.

The temperature measuring apparatus 40 is, in this example, executed as a surface temperature detecting unit 42 and consists, as shown in FIGS. 6A and 6B, of an arrangement of several temperature sensors 43 which are arranged in a housing 44 in such a manner that one of the temperature sensors 43 is associated with each of the tensile supports 51. A guide roller 45 positions the support means 5 so that the orientation of the tensile supports 51 relative to the temperature sensors 43 is guaranteed. The surface temperature detecting unit 42 is fastened in such a manner that in the case of travel of the elevator over its entire range of movement the points of the support means 5 with the most loading can be guided past the surface temperature detecting unit 42 and thus the surface temperatures measured. The surface temperature detecting unit 42 transmits the measurement results to the checking unit 32. A position transmitter 33, as shown in FIG. 4, transmits the respective position of the elevator car 2 or of the counterweight 3 directly, or by means of an installation control or elevator control 35, to the checking unit 32. The checking unit 32 comprises, in particular, or at least controls, the switching element 31, the current control 30 and apparatus for measuring the measuring current, for storage of the measurement data, as well as an evaluating unit 34 for evaluating the measurement results. In case of need a communications interface with respect to the installation control 35 is present, which can communicate installation-specific characteristic data. Moreover, it contains the mains supply units required for operation of the checking unit as well as input and output apparatus.

The checking unit 32 switches, in a first step, the switching element 31 to a first tensile support pair $51_1$, $51_{n/2+1}$ and establishes the requisite supply voltage and compares this supply voltage with the required supply voltage established within the scope of the new installation. The checking unit 32 now initializes a first measuring travel, for example by means of a signal to the elevator control 35 or by means of a release signal to the operative. The checking unit 32 during the measuring travel records the measurement results of the surface temperature detecting unit 42 or the surface temperature of the connected tensile supports $51_1$, $51_{n/2+1}$, the precise respective position of the car 1 as well as if need be the status of the measuring current or the supply voltage.

After termination of the first measuring step the checking unit 32 switches by means of the switching element 31 to a next tensile support pair $51_2$, $51_{n/2+2}$ and repeats the measurement sequence in correspondence with the measurement sequence of the first tensile support pair $51_1$, $51_{n/2+1}$. The measurements are continued until all of the tensile supports 51 are checked. Finally, the checking unit 32 creates a concluding log which records deviations from the target state, wherein the target state corresponds with the new state inclusive of the anticipated deviations dependent on age or caused by tolerances.

In this example setting of the measuring current takes place automatically at the current control, the switching to the tensile support takes place automatically and the measuring of the temperature as also the evaluation take place automatically. The illustrated variant represents an automated overall solution by means of which checking of the support means 5 of a elevator installation 1 can be undertaken with minimal cost of personnel. The result is stored in reproducible manner. The arrangement can be temporarily used as a maintenance tool or it can be permanently left as a component of the elevator installation, whereby measurements are made possible at short intervals. This is particularly advantageous in the case of installations which are very strongly loaded or installations with, for example, influences which can be difficult to check, such as can be present, for example, in a chemically aggressive environment.

The solution shown in FIGS. 3 and can be combined. Thus, for example, the positional recognition of the car illustrated in FIG. 4 can be omitted. Partly manual checking sequences result therefrom.

The tensile supports 51 are switchable independently of the installation data and the selected checking procedure. In FIG. 3 every one of the tensile supports 51 is individually switched and individually checked. The tensile supports 51 are electrically connected together at the one support means end 20. This solution requires few apparatus and can be carried out in simple manner. In FIG. 4 in each instance two of the tensile supports 51 are connected together in series in that the corresponding tensile supports 51 are electrically connected at the second support means end 20. This solution allows checking of two tensile supports at the same time and accordingly requires less expenditure of time for carrying out the checking.

Figure 5:
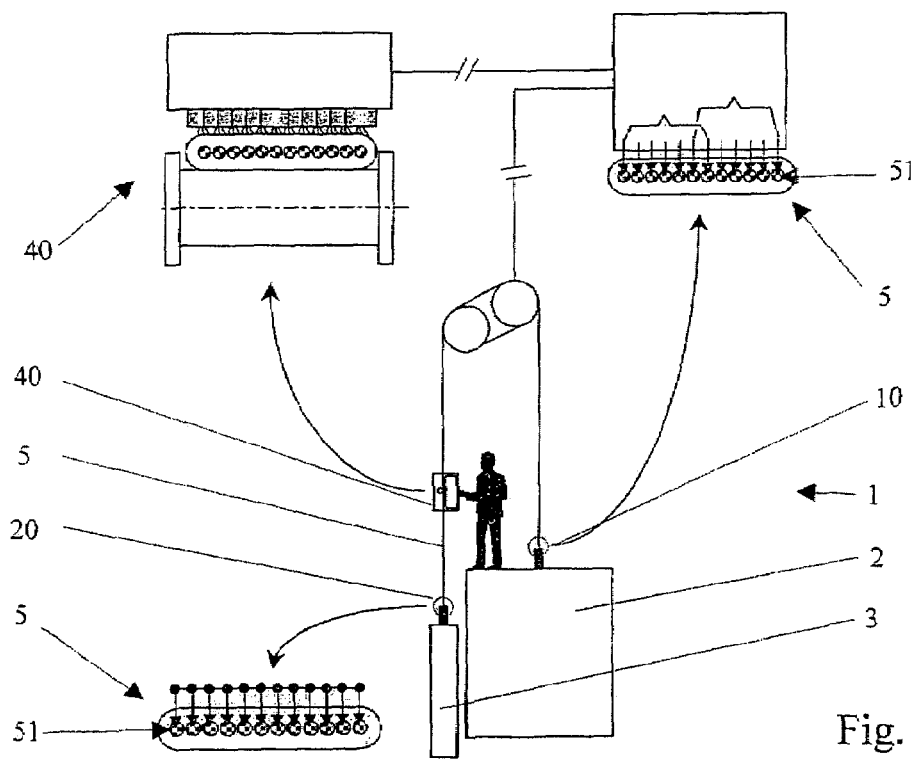
FIG. 5 is a schematic diagram of a further example of equipment for establishing the readiness for discard of a support means in an elevator installation with 1:1 suspension.

In FIG. 5, similarly each time two of the tensile supports 51 are connected together in series. All tensile supports 51 are electrically connected at the second support means end 20 and the selection of the connected-together tensile supports 51 is carried out by the corresponding switch setting at the first support means end 10. In this solution as well the checking of two tensile supports 51 is allowed at the same time and accordingly requires less expenditure of time for carrying out the checking. By contrast to the solution according to FIG. 1, there are yielded different results, which are to be evaluated, for possible parallel connections of the tensile supports 51.

The illustrated solutions represent variants which can be expanded by the expert so that, for example, several tensile supports of the support means are checked each time individually in succession in time or that several tensile supports of the support means are connected together to form groups and are checked in groups in succession in time or that, for example, all tensile supports of the support means are connected together to form a group and are checked together.

Instead of the switching element 31, the tensile supports can be directly connected without the switching element.

In FIG. 5 there is shown an elevator installation 1 with a directly suspended car 2 or counterweight 3. By way of example, the temperature measuring apparatus 40 is placed on the car. In the individual case several different placements of the temperature measuring apparatus 40 can be feasible in order to be able to check the support means 5 over the entire length thereof or the expert arranges the temperature measuring device as desired at the point or points at which the support means experiences its greatest loading. The points of greatest loading are, for example, the length sections of the support means which experience the most reverse bending with consideration of use of the installation.

Figures 7A, 7B:
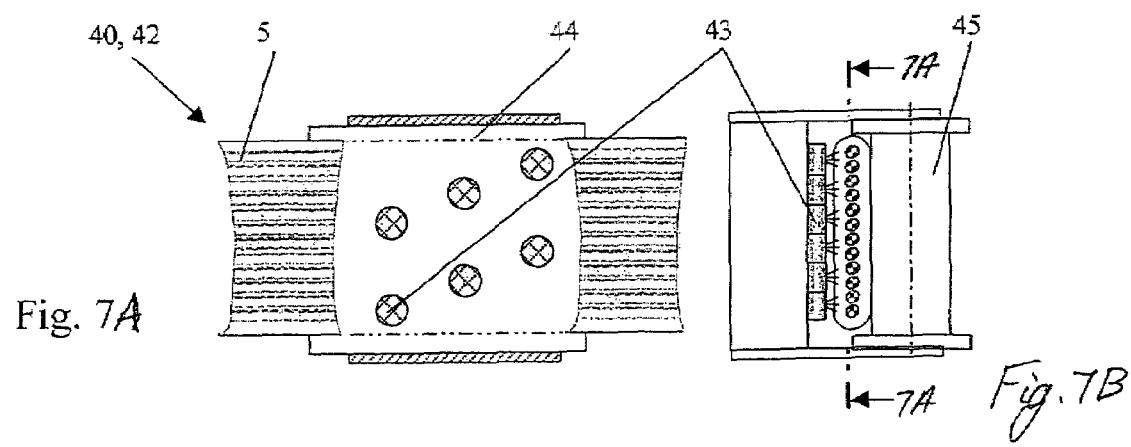
FIG. 7A is a cross-sectional view taken along the line 7A—7A in FIG. 7B showing a further example of a temperature measuring apparatus according to the present invention for establishing the surface temperature of a support means.

FIG. 7 shows an alternative arrangement of the temperature sensors 43 on the surface temperature detecting unit 42. In this connection the temperature sensors 43 are placed in such a manner that one of the temperature sensors 43 can detect two or several of the tensile supports 51. Thus a cost saving is produced, since the number of temperature sensors 43 can be significantly reduced.

The expert will recognize further advantageous combinations. Thus, the expert uses, for example, a thermal imaging camera as a temperature measuring apparatus, the expert detects the connection together of the tensile supports, i.e. individually or in groups, which is most advantageous for the expert, the expert determines the degree of automation of the control sequence or the expert ascertains the optimum arrangement of the temperature measuring apparatus.

In the case of use on a stationary support means the temperature measuring apparatus is guided in suitable manner along the support means run.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. Equipment for checking a support means, the support means including a tensile support formed at least partly of an electrically conductive material, and the tensile support being provided with a sheathing covering the tensile support, comprising:
    a current control connected to the tensile support and causing an electrical measuring current flow through the tensile support at least periodically;
    a temperature measuring apparatus measuring a temperature of the support means whereby a damage state of the tensile support is determined based upon the measured temperature; and
    a position transmitter for generating a signal representing a position along the support means at which said temperature measuring apparatus is measuring the temperature.

2. The equipment according to claim 1 wherein said current control generates the electric current with at least one of variable magnitude and variable pulse duration.

3. The equipment according to claim 1 wherein the support means includes at least two of the tensile supports and including a switch element for selective connection of the tensile supports to be checked to said current control.

4. The equipment according to claim 1 wherein said temperature measuring apparatus is one of a surface thermometer, a surface temperature detecting unit and a thermal imaging camera.

5. The equipment according to claim 1 including a checking unit connected to said temperature measuring apparatus and adapted to be connected to an elevator installation control.

6. The equipment according to claim 1 including an evaluating unit connected to said temperature measuring apparatus for evaluating the measured temperature.

7. A method of checking a support means, the support means including a tensile support that is at least partly formed of an electrically conductive material, and the tensile support being provided with a sheathing covering the tensile support, comprising the steps of:
    a) causing an electrical measuring current to flow through the tensile support at least periodically;
    b) measuring a temperature of the support means; and
    c) determining a damage state of the tensile support based upon the measured temperature wherein when placing the support means in operation a requisite new voltage for attainment of the measuring current of the tensile support is established and when performing said step a) a requisite supply voltage for attainment of the measuring current in relation to the new voltage is assessed.

8. The method according to claim 7 including determining a general state of the support means based upon a relationship between the new voltage and the supply voltage.

9. The method according to claim 7 wherein the support means includes a plurality of individual tensile supports and including performing said steps a) through c) sequentially for each the tensile supports.

10. A method of checking a support means, the support means including a tensile support that is at least partly formed of an electrically conductive material, and the tensile support being provided with a sheathing covering the tensile support, comprising the steps of:
    a) causing an electrical measuring current to flow through the tensile support at least periodically;
    b) measuring a temperature of the support means by establishing the temperature of the support means per length section of the support means, each length section being associated with at least one of a corresponding temperature change $\Delta T$ with respect to the preceding length section and a mean value of the temperature measurements over the entire support means length; and c) determining a damage state of the tensile support based upon the measured temperature.

11. The method according to claim 10 wherein said step b) is performed by measuring the temperature substantially at the surface of the sheathing of the support means.

12. The method according to claim 10 further including a step of generating a warning report when the temperature change ΔT falls below or exceeds a predefined value.

13. The method according to claim 10 wherein local damage to the support means is indicated by the temperature change ΔT thereby establishing readiness of the support means for discard.

14. The method according to claim 10 wherein a reduction in load-bearing force of the tensile support is indicated by the temperature change ΔT thereby establishing readiness of the support means for discard.

15. The method according to claim 10 wherein the support means includes a plurality of individual tensile supports and including performing said steps a) through c) sequentially for each the tensile supports.

16. The method according to claim 10 wherein when placing the support means in operation a requisite new voltage for attainment of the measuring current of the tensile support is established and when performing said step a) a requisite supply voltage for attainment of the measuring current in relation to the new voltage is assessed.

17. The method according to claim 16 including determining a general state of the support means based upon a relationship between the new voltage and the supply voltage.

* * * * *